(12) United States Patent
Chen et al.

(10) Patent No.: US 9,763,630 B2
(45) Date of Patent: Sep. 19, 2017

(54) STEREOSCOPIC IMAGING SYSTEMS AND METHODS

(71) Applicant: Nuctech Company Limited, Beijing (CN)

(72) Inventors: Zhiqiang Chen, Beijing (CN); Zhuowen Tu, Beijing (CN); Liang Li, Beijing (CN); Ziran Zhao, Beijing (CN); Duokun Zhang, Beijing (CN); Zhi Peng, Beijing (CN); Jin Cui, Beijing (CN); Dong Lin, Beijing (CN)

(73) Assignee: Nuctech Company Limited, Beijing (CN)

( * ) Notice: Subject to any disclaimer, the term of this patent is extended or adjusted under 35 U.S.C. 154(b) by 283 days.

(21) Appl. No.: 14/525,078

(22) Filed: Oct. 27, 2014

(65) Prior Publication Data

US 2015/0117602 A1    Apr. 30, 2015

(30) Foreign Application Priority Data

Oct. 29, 2013 (CN) .......................... 2013 1 0521748

(51) Int. Cl.
*A61B 6/02* (2006.01)
*G06T 15/08* (2011.01)
(Continued)

(52) U.S. Cl.
CPC ............ *A61B 6/022* (2013.01); *A61B 6/4266* (2013.01); *G06T 15/08* (2013.01);
(Continued)

(58) Field of Classification Search
CPC .. A61B 6/00; A61B 6/02; A61B 6/022; A61B 6/42; A61B 6/4266; A61B 6/52;
(Continued)

(56) References Cited

U.S. PATENT DOCUMENTS

| 5,493,595 A | * | 2/1996 | Schoolman | ............ | A61B 6/462 |
| | | | | | 348/E13.008 |
| 8,619,082 B1 | * | 12/2013 | Ciurea | ............... | H04N 13/0242 |
| | | | | | 345/427 |

(Continued)

FOREIGN PATENT DOCUMENTS

| DE | 102004022427 A1 | 12/2005 |
| FR | 2919780 | 2/2009 |
| GB | 2454047 | 4/2009 |

OTHER PUBLICATIONS

European Search Report in European Application No. EP 14190459, dated Mar. 10, 2015.

(Continued)

*Primary Examiner* — Anastasia Midkiff
(74) *Attorney, Agent, or Firm* — Knobbe Martens Olson & Bear LLP (57) ABSTRACT

A stereoscopic imaging system and method is disclosed. In one aspect the system includes an X-ray source that emits a plurality of X-ray fanbeams. The system includes columns of detectors. Each column of detectors is arranged at a preset angle with respect to the X-ray source. The detectors detect a strength of an X-ray fanbeam penetrating an object under inspection. The detectors form transmission images when the object intersects, or moves along a direction intersecting with, the X-ray fanbeams. The system includes a reconstruction apparatus that uses any two of the formed transmission images as a binocular image. The reconstruction apparatus calculates depth information of the object on the transmission images. The reconstruction apparatus superposes and fuses the calculated depth information to obtain 3D information. The reconstruction apparatus performs 3D reconstruction so that the detected object can be presented in a stereoscopic manner from different view angles.

14 Claims, 6 Drawing Sheets

(51) Int. Cl.
*H04N 13/00* (2006.01)
*A61B 6/00* (2006.01)
*G01V 5/00* (2006.01)

(52) U.S. Cl.
CPC ....... *H04N 13/0007* (2013.01); *G01V 5/0058* (2013.01); *G06T 2207/20212* (2013.01); *H04N 2213/003* (2013.01)

(58) Field of Classification Search
CPC ....... A61B 6/5205; A61B 6/5211; G06T 7/00; G06T 7/0022; G06T 7/0051; G06T 7/0065; G06T 7/0075; G06T 15/00; G06T 15/08; G06T 2207/00; G06T 2207/10; G06T 2207/10116; G06T 2207/20; G06T 2207/20212; G06T 2207/20221; G01N 23/00; G01N 23/02; G01N 23/04; G01N 23/06; G01N 23/08; G01N 23/083; H04N 13/00; H04N 13/0003; H04N 13/0007; H04N 13/0055; H04N 13/0059; H04N 13/0074; H04N 13/0081; H04N 13/02; H04N 13/0271; H04N 2213/00; H04N 2213/003

See application file for complete search history.

(56) References Cited

U.S. PATENT DOCUMENTS

| | | | |
|---|---|---|---|
| 2006/0170674 A1 | 8/2006 | Tsubaki et al. | |
| 2009/0315982 A1* | 12/2009 | Schmidt | H04N 13/0025 348/47 |
| 2010/0040196 A1* | 2/2010 | Zhang | A61B 6/022 378/42 |
| 2013/0135435 A1* | 5/2013 | D'Amato | H04N 13/0022 348/43 |

OTHER PUBLICATIONS

Evans, et al. "A new stereoscopic X-ray imaging technique using a single X-ray source: theoretical analysis." NDT&E International, 1996, No. 1, pp. 27-35, vol. 29, Elsevier Science Ltd., Great Britain.

* cited by examiner

STEREOSCOPIC IMAGING SYSTEMS AND METHODS

CROSS-REFERENCE TO RELATED APPLICATIONS

This application claims priority to Chinese Application No. 201310521748.1, filed on Oct. 29, 2013, entitled "STEREOSCOPIC IMAGING SYSTEM AND METHODS," which is incorporated herein by reference in its entirety.

BACKGROUND

Technological Field

The disclosed technology relates to radiography, and particularly to stereoscopic imaging systems and methods using a single source and multiple detectors.

Description of the Related Technology

Safety inspection plays an important role in various fields such as campaigns against terrorism, drug trading, and trafficking. Countries around the world have paid more attention to safety inspection in public sites, and imposed stricter requirements on customs inspection of containers, luggage and the like.

Radiography systems used for applications including safety inspection produce two dimensional (2D) transmission images using linear detectors. Such detected images are difficult to interpret due to a lack of depth information for observed objects, and substantial overlapping of projections. Thus, there is a need for stereoscopic imaging systems and methods that enable better recognition and identification of objects.

SUMMARY OF CERTAIN INVENTIVE ASPECTS

The disclosed technology relates to stereoscopic imaging systems and methods that overcome one or more problems with the conventional technology.

One aspect of the disclosed technology is a stereoscopic imaging system. The system includes an X-ray source configured to emit a plurality of X-ray fanbeams. The system includes a plurality of columns of detectors, wherein each column of detectors is arranged at a preset angle with respect to the X-ray source. The plurality of columns of detectors are configured to detect a strength value of a respective one of the X-ray fanbeams penetrating an object under inspection and form a respective transmission image, when the object intersects, or moves along a direction intersecting with, the X-ray fanbeams. The system includes a reconstruction apparatus configured to use any two of the formed transmission images as a binocular image. The reconstruction apparatus is configured to calculate depth information of the object on the transmission images. The reconstruction apparatus is configured to superpose and fuse the calculated depth information to obtain 3-Dimensional (3D) information. The reconstruction apparatus is configured to perform 3D reconstruction.

Another aspect of the disclosed technology is a method of stereoscopic imaging in a stereoscopic imaging system. The stereoscopic imaging system includes an X-ray source and a plurality of columns of detectors. Each column of detectors is arranged at a preset angle with respect to the X-ray source. The method includes emitting a plurality of X-ray fanbeams. The method includes detecting, by each column of detectors, a strength value of a respective one of the X-ray fanbeams penetrating an object under inspection when the object intersects, or moves along a direction intersecting with, the X-ray fanbeams. The method includes forming, by each column of detectors, a respective transmission image. The method includes using any two of the formed transmission images as a binocular image. The method includes calculating depth information of the object on the transmission images. The method includes superposing and fusing the calculated depth information to obtain 3-Dimensional (3D) information. The method includes performing 3D reconstruction.

Through 3D reconstruction using transmission images collected by a plurality of columns of linear detectors at certain angles, the lost depth information in the transmission images can be recovered so that the detected object is presented in a stereoscopic manner from different view angles. This facilitates better image analysis.

BRIEF DESCRIPTION OF THE DRAWINGS

The following figures illustrate implementations of the disclosed technology. The figures and implementations provide some embodiments of the disclosed technology in a non-limiting and non-exclusive manner.

DETAILED DESCRIPTION OF CERTAIN ILLUSTRATIVE EMBODIMENTS

The following detailed description is directed to certain specific embodiments of the disclosed technology. However, the disclosed technology can be embodied in a multitude of different ways. It should be apparent that the aspects herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using other structure, functionality, or structure and functionality in addition to or other than one or more of the aspects set forth herein.

The described embodiments are just intended for illustrating rather than limiting the disclosed technology. Numerous specific details are illustrated for a clear and thorough understanding of the disclosed technology. It is apparent to those skilled in the art that these specific details are not necessary for implementation of the disclosed technology. Detailed description of known structures, circuits, materials or methods are omitted which otherwise may obscure the disclosed technology.

Throughout the specification, reference to "an embodiment," "embodiments," "an example" or "examples" means that particular features, structures or characteristics described in connection with such embodiment or example are contained in at least one embodiment of the disclosed technology. The phrase "an embodiment," "embodiments," "an example" or "examples" in various places throughout the specification does not necessarily refer to the same embodiment or example. Further, the particular features, structures or characteristics may be contained in one or more embodiments or examples in any appropriate combination and/or sub-combination. Those skilled in the art will appreciate that the term "and/or" herein indicates any or all combinations of one or more of the listed items.

3D images are widely used in people's daily lives. Compared with 2D images, 3D images can better depict real scenes and achieve more vivid visual effects. In the radiography field, CT imaging can reconstruct a 3D structure of an object. However, 3D CT imaging has disadvantages that scanning devices have very complex structure, measurement requires a long time, and so on. In addition to scientific contribution, stereoscopic imaging technology from multiple view angles in transmission images has good application prospect. The stereoscopic imaging technology from multiple view angles in transmission images can give an approximate 3D image. When presented with small-angle rotation or on a 3D display terminal 3D images may provide an inspector with a stereoscopic perception, and enhance his or her ability to detect and identify objects.

Embodiments of the disclosed technology use 3D reconstruction of transmission images collected by a plurality of columns of linear detectors at certain angles to recover lost depth information in the transmission images so that the detected object is presented in a stereoscopic manner from different view angles. This facilitates better image analysis. For example, in safety inspection of containers, the container may be scanned with X rays without opening the container. Then, 3D information of part of the container may be restored for presentation in a new manner to detect and identify objects.

Figure 1:
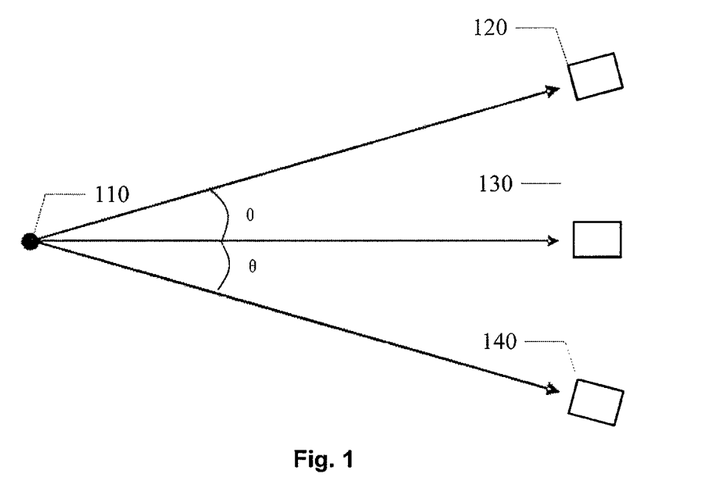
FIG. 1 illustrates an exemplary top view of an image capturing system according to embodiments of the disclosed technology.
Figure 11:
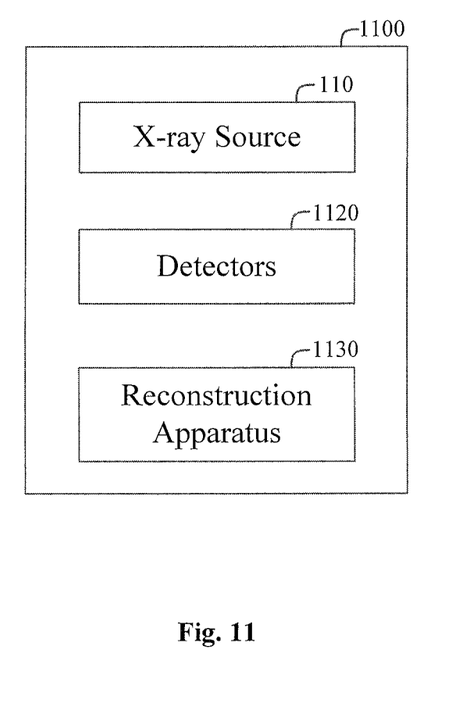
FIG. 11 is a functional block diagram of an image system from one or more of the embodiments of the disclosed technology.

According to embodiments of the disclosed technology, a stereoscopic imaging system as shown in FIG. 11 is provided including an X-ray source 110, a plurality of columns of detectors 1120, and a reconstruction apparatus 1130 implemented by a processor or computer. The X-ray source 110 is configured to emit a plurality of X-ray fanbeams. Each column of detectors (for example, 120, 130, 140) of the plurality of detectors 1120 is arranged at a preset angle with respect to the X-ray source 110, and configured to detect a strength value of a respective one of the X-ray fanbeams penetrating an object under inspection and form a respective transmission image, when the object intersects, or moves along a direction intersecting with, the X-ray fanbeams. The reconstruction apparatus 1130 is configured to use any two of the formed transmission images as a binocular image, calculate depth information of the object on the transmission images, superpose and fuse the calculated depth information to obtain 3D information, and perform 3D reconstruction FIG. 1 shows a top view of an image capturing system. There are three viewing angles shown in the figure. This is exemplary, and more viewing angles may be used according to requirements of practical applications. X-ray fanbeams from the X-ray source 110 to the three (i.e., left 120, middle 130, and right 140) columns of detectors have a preset beam angle between them, such as an angle θ between the X-ray fanbeams emitted to the left 120 and middle 130 columns of detectors, and the same angle θ between the X-ray fanbeams emitted to the right 140 and middle 130 columns of detectors. Three images scanned at different angles are then obtained. The middle X-ray fanbeam is along a main beam direction, and the left and right X-ray fanbeams are symmetrically located at both sides of the main beam. Although three viewing angles are used in this embodiment, the image capturing system 1100 and reconstruction apparatus 1130 may use more viewing angles by adding pairs of viewing angles at both sides of the main beam in a symmetric manner.

Figure 2:
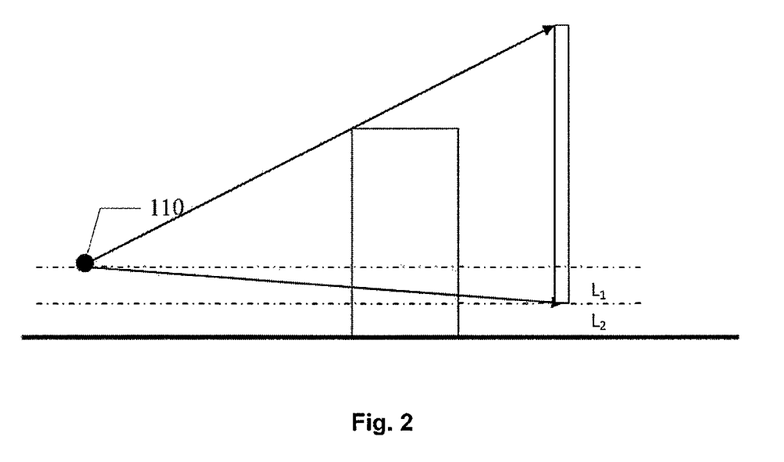
FIG. 2 illustrates an exemplary side view of the image capturing system from FIG. 1.

FIG. 2 shows a side view of an image capturing system 1100. The capturing system primarily includes the X-ray source 110, a collimation apparatus (not shown), and a data collection system (not shown). When the object under inspection passes a detection area at a velocity, a number of images will be generated simultaneously, and the number of images are equal to the number of detector columns. An appropriate reference coordinate system may be establish in this imaging model to facilitate 3D reconstruction by reconstruction apparatus 1130 and multi-angle viewing of the obtained images at multiple viewing angles.

Figure 3:
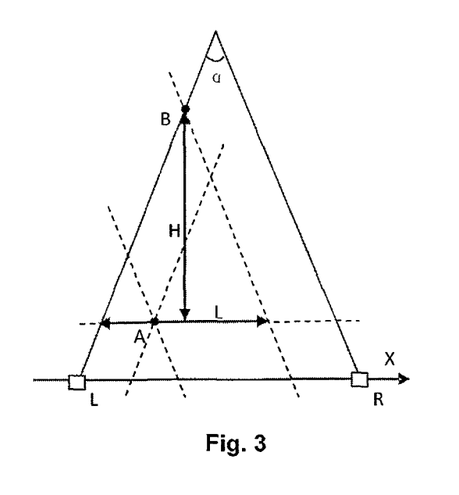
FIG. 3 is a schematic diagram depicting an exemplary process of calculating depth information.

FIG. 3 shows the principle for calculating depth information by using two images at different viewing angles, used by reconstruction apparatus 1130. There may be a difference between positions of objects having different depths in the two images, and the depth information can be acquired with such position difference. Assume that there are two points A and B at different depths, and the point B is on the right of the point A in the right detector-scanned image, while the point B is on the left of the point A in the left detector-scanned image. The relative position difference between the two points is L, and the depth difference between the two points A and B may be calculated with L and a beam angle α as follows:

$$H = \frac{L}{2\tan\frac{\alpha}{2}}$$

When the beam angle α is very small, $$H \approx \frac{L}{\alpha}$$

i.e., the relative depth between the objects is in proportion to the relative position difference between the objects in the left and right images.

The depth information of the objects on any two of the images captured at different viewing angles can be calculated by combining the two images. The calculated 3D information may be superposed and fused to restore 3D information as much as possible. In the example using three viewing angles, three images can be captured at the same time as left, middle and right images. There are three combinations of any two of the images. In the case of combining the left and right images, the coordinate system of one of the two images may be used as a reference coordinate system, and 3D coordinates may be calculated with the following formula:

$$z = L - \frac{v}{2 \cdot f \cdot \tan\frac{\alpha}{2}} \cdot \Delta x$$

Here, v represents the velocity at which the object passes the scan area, f represents a frequency at which X-rays are emitted, α is an angle sandwiched between the two viewing angles of the two images, and Δx represents a difference between positions of a single feature point in the different images. L denotes a distance from the X-ray source to a plane in which the detectors are arranged. With the left image being a reference image, the x and y coordinates may be modified using the calculated depth information z as follows:

$$y = y_i - \frac{z \cdot (y_i \cdot dy - L_2)}{L}$$
$$x = x_i - z \cdot \tan\frac{\alpha}{2}$$

Here, $x_i$, $y_i$ are coordinates of a point in the images, and dy represents a resolution in the y direction. Calculation methods similar to the above may be used for the other combinations of images, except that the formulas for coordinate calculation and modification need to be appropriately adapted.

Further, there may be geometric distortion along the column direction, and it is thus necessary to perform geometric correction in the column direction. Causes and correction methods of such geometric distortion will be detailed below.

Parameters such as device position and beam angle are relatively fixed during the image capturing process, and thus it is unnecessary to consider a process similar to a calibration process for an optical image. Selection of suitable reference coordinate system will suffice.

According to some embodiments of the disclosed technology, point-to-point matching, by reconstruction apparatus 1130, between two images captured at different viewing angles may be obtained by: first establishing a correspondence between a feature point in one of the images and the corresponding point in the other image, by means of conventional methods for feature extraction and matching; then establishing Hilbert Kernels centered on the feature points, and a Hilbert Space by superposition; and iteratively calculating a smooth spatial vector field by using a spatial smoothness constraint. This spatial vector field represents the point-to-point correspondence between the two images.

Alternatively, the algorithm SIFT Flow may be used to obtain the point-to-point correspondence between two images. The principle of SIFT Flow is first calculating a SIFT eigenvector, Dense SIFT, for each pixel in the images, and then matching a description of the SIFT vectors using a flow estimation algorithm. The algorithm SIFT Flow equally treats all pixels in the images to be matched, thereby ignoring difference between pixels. each pixel in an image may have a different amount of information. Salient pixels for an object in the image generally have a larger amount of information, while pixels in background (e.g., a background in pure black) have a smaller amount of information. If all the pixels are treated equally, matching values of pixels containing no or little information may influence matching values of important pixels. This incurs disturbance in matching process, and leads to an overall inaccurate result. The disclosed technology, however, employs an improved energy function which can increase contribution of areas having a larger amount of information, and weaken contribution of background areas. Accordingly, it is possible to prevent the match process from being influenced by the background area, and facilitate obtaining of more accurate matching result. Moreover, the algorithm Belief Propagation may be used to optimize a target function to calculate an optimized flow field, which represents a correspondence between two images.

Figure 4:
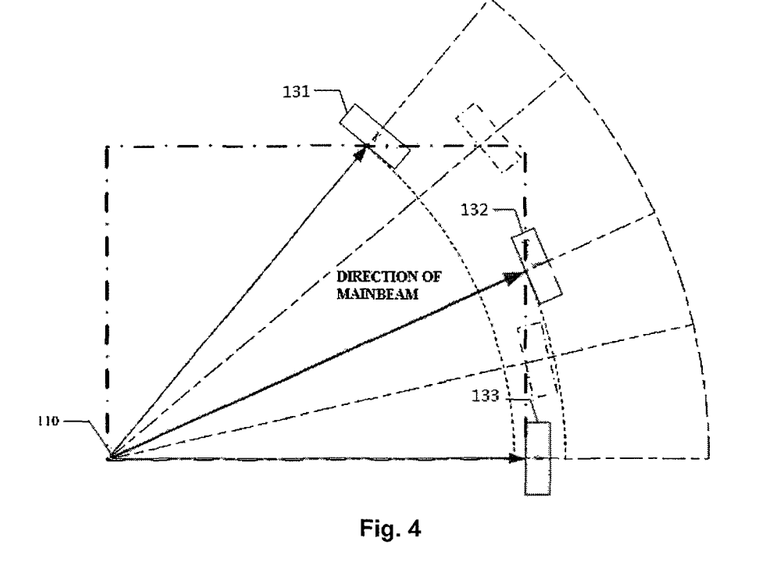
FIG. 4 is a schematic diagram depicting an exemplary layout along a column direction of detectors.

Since X rays are emitted in a radial pattern, the linear detectors may be arranged in a fan-shape (or arc-shape) layout to accommodate the emission pattern of X rays and thus reduce geometric distortion. For some embodiments, the detectors 1120 are arranged in a fan-shape (or arc-shape) layout. In some embodiments, the layout approximates a fan (or arc) shape due to mechanical architecture and available space. FIG. 4 shows an example of the detector layout. The detectors may be installed linearly on either a vertical arm support or a horizontal arm support, or both of them, i.e., L-shape arm support. For example, a L-shape column of detectors includes a plurality of detector modules 131, 132, and 133 for receiving X-ray beams emitted from the X-ray source 110. The angle between the two arm supports can be adjusted. Although some embodiments employ the L-shape arm support, other embodiments use other layouts according to requirements of mechanical architecture for the application. Embodiments that approximate a fan (or arc) shape results in a change in radius of the fan shape. For these embodiments geometric distortion in the column direction may be reduced, if not eliminated. Geometric distortion may affect 3D reconstruction, and it is thus necessary to perform geometric correction in the reconstruction process.

Figure 5:
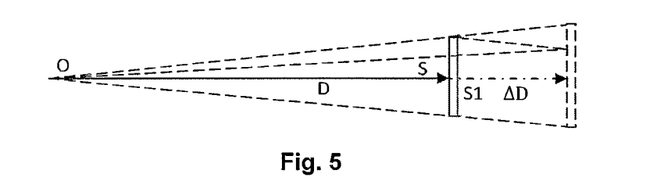
FIG. 5 is a schematic diagram depicting an exemplary process for geometric correction along the column direction.

FIG. 5 shows the principle of geometric correction used by reconstruction apparatus 1130. Given a size S in the column direction, and a number N of detectors, the resolution in the direction of X-ray main beam is S/N, which is considered as a standard resolution. A distance from the X-ray source O to the detector modules in the main-beam direction is D, that is, the fan radius is D. For any of the other modules, the distance varies by ΔD. For each of these different modules, ΔD can be obtained based on the layout of the detectors, the size Si with respect to the module in the main-beam direction is $$\frac{D}{D + \Delta D} \cdot S,$$

and the resolution is $$\frac{S}{N} \cdot \frac{D}{D + \Delta D}$$

Based on the difference in resolution, geometric correction in the column direction can be performed using a method of image differencing.

Figure 6:
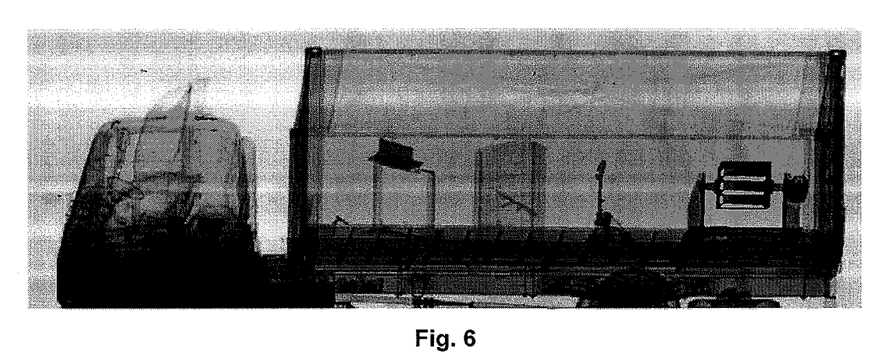
FIG. 6 shows a schematic diagram of a container truck.

FIG. 6 shows a container truck under inspection, and is one of the three images captured in the above embodiment.

Figure 7:
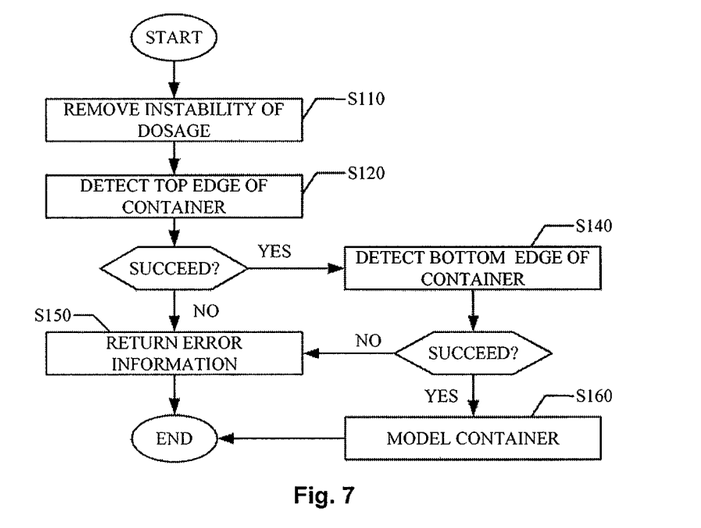
FIG. 7 shows an exemplary process of identifying and modeling a container.

Goods in the container are of interest. The container itself is a regular cube. The 3D information of the container itself can be restored by reconstruction apparatus 1130 by performing 3D modeling. The obtained 3D information may be used as a reference for 3D reconstruction of the goods within the container. FIG. 7 shows a process used by reconstruction apparatus 1130 of position identification and modeling of the container as explained below.

At step S110, influence caused by instability of dosage is eliminated.

The influence on the algorithm from instability of dosage is eliminated by using prior information.

$$U_x = -\log(I/\alpha)$$

Here, $\alpha$ represents an air value for a current column which is capturing an image (i.e., an image captured when there is only air in the relevant area), and I represents a reading of a detector in the current column. The transformed image gray value $U_x$ is insensitive to instability of dosage.

A top edge is detected at step S120.

In an example, the top edge of the container may be detected using a morphological method to calculate a morphological gradient, and using the Hough transform. If no top edge is detected, an error is returned at step S150.

At step S140, the head part of the truck is removed, leaving only the container part.

The upper edge of the chassis in the truck is detected in the same way as detection of the top edge of the container. Then, the exact position and size of the container can be obtained after detection of the container top edge and the chassis upper edge.

At step S160, the container is modeled.

By using the obtained position and size of the container, the type of the container is determined, and accordingly a suitable 3D model is selected from a template library, which will be imported in 3D reconstruction.

For a container truck under safety inspection, the truck part is generally of less importance. 3D information of the truck part may be restored quickly and effectively by using a modeling method. The position and size of the truck part are first identified as features, and then a best 3D template for the truck part is found in a template library.

Figure 8:
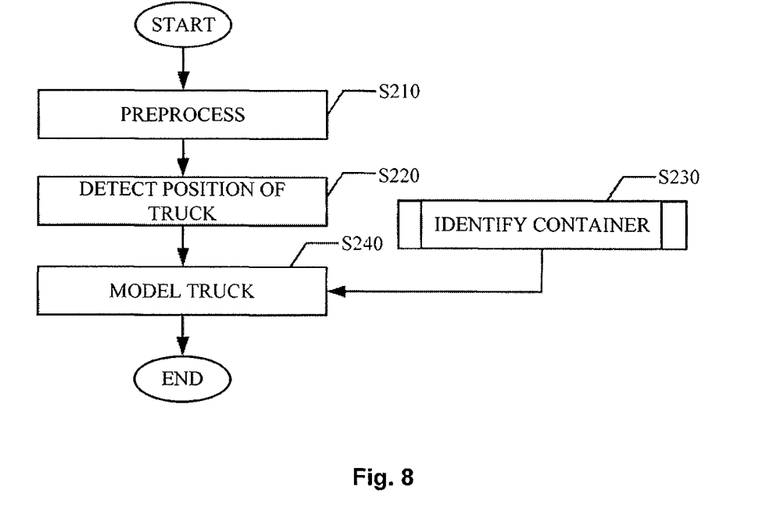
FIG. 8 shows an exemplary process of modeling a truck body.

FIG. 8 shows a process of identifying and modeling the truck part used by reconstruction apparatus 1130. In the disclosed technology, the position of the truck part in an image is identified mainly based on edge information. Given that the container has been identified, the type of the truck and the position of the truck head are identified. To obtain a robust result, detection of the truck position may be performed in three steps: pre-processing of strip removal to obtain an image with a gentle change in background; calculating gradients and quantizing a map of the gradients to remove influence from small gradient fluctuations; and locating an maximal continuous area (i.e., the truck position) of horizontal and vertical projections in the binarized gradient map.

At step S210, the pre-processing of strip removal includes removing strips in each of horizontal and vertical directions. In the horizontal direction, a sequence of projections of the image in the vertical direction is first acquired. Each projection is subjected to median filtering, and the image line corresponding to the projection is determined as a stripe if there is a large difference before and after the filtering. Values in the image line are replaced with those of the closest, non-stripe image line.

At step S220, the gradients are obtained by quantizing the image and then calculating the gradients.

The truck position is obtained by calculating projections in horizontal and vertical directions with respect to the gradient map, and detecting a maximal continuous area after subtracting the minimal value (i.e., removing any stripe which possibly remains). This detected area represents the truck position.

At step S230, the container is identified as described above.

At step S240, with the container having been identified, the position and orientation of the truck are determined by identifying the truck part. The 3D model of the truck from the template library can be used as the truck part during 3D reconstruction.

Figure 9:
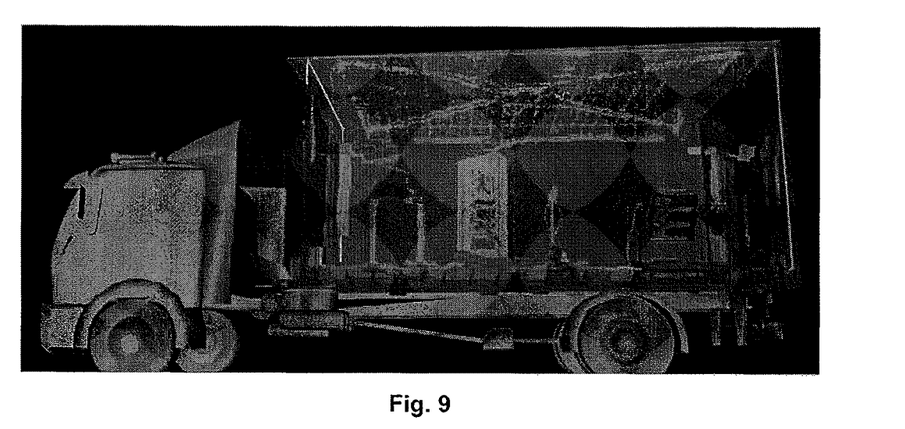
FIG. 9 a schematic diagram showing 3D reconstruction result according to embodiments of the disclosed technology.

In the safety inspection industry, stereoscopic reconstruction from transmission images is for the purpose of assisting in inspection, and accurate measurement is not required. Accordingly, the disclosed technology focuses on rendering a stereoscopic visualization of transmission images by using depth information contained in the transmission images. The purpose is to distinguishably display the images of objects overlapped with each other. The stereoscopic visualization may be presented in two approaches. The first approach is to use a 3D presentation tool, such as OpenGL, to develop 3D presentation software which provides a 3D effect by rotation at different angles. The second approach is using a hardware presentation terminal. In the disclosed technology, a 3D display for naked eye is used to display 3D data. FIG. 9 depicts a result of 3D reconstruction presented via OpenGL software kit.

With the above embodiments, a method for assisting in inspection is provided by rendering a stereoscopic visualization of transmission images at different viewing angles based on depth information calculated from the transmission images. Further, the 3D modeling of the container is implemented with modeling techniques to improve accuracy in 3D reconstruction. Third, the 3D modeling of the truck is implemented with modeling techniques to enhance 3D presentation.

In addition, the 3D presentation can be provided at different angles by using presentation software. The 3D presentation can be further enhanced in conjunction with hardware presentation terminal.

Figure 10:
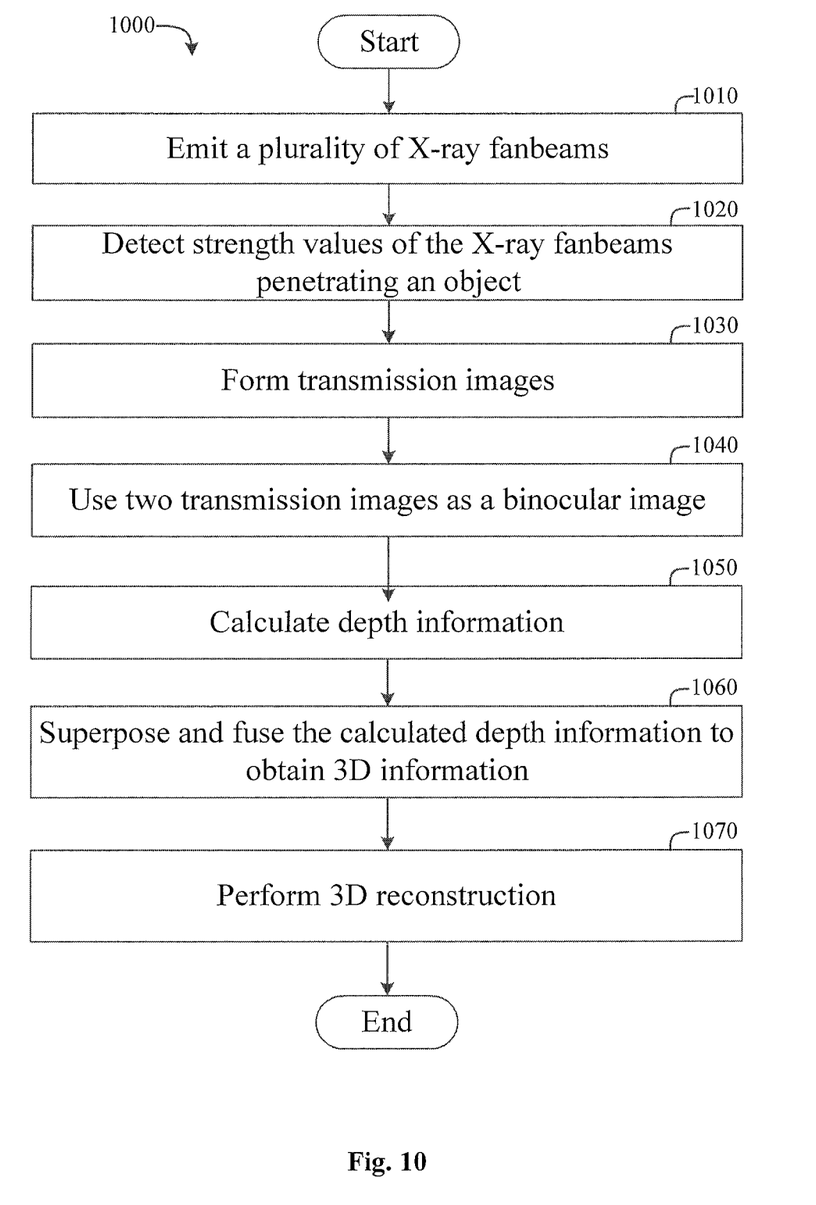
FIG. 10 is a flowchart illustrating a method of stereoscopic imaging according to the disclosed technology.

A method of stereoscopic imaging in a stereoscopic imaging system according to the disclosed technology depicted in FIGS. 1-9 and 11, will now be described with respect to FIG. 10, which is a flowchart illustrating a method 1000 of stereoscopic imaging. The stereoscopic imaging system may comprise an X-ray source 110 and detectors 1200, such as a plurality of columns of detectors 120, 130, and 140, wherein each column of detectors (120, 130, 140) is arranged at a preset angle with respect to the X-ray source 110. At block 1010, method 1000 emits a plurality of X-ray fanbeams. At block 1020, method 1000 detects strength values of the X-ray fanbeams penetrating an object. At block 1030, method 1000 forms transmission images. At block 1040, method 1000 uses two transmission images as binocular images. At block 1050, method 1000 calculates depth information. At block 1060, method 1000 superposes and fuses the calculated depth information to obtain 3D information. At bloc 1070, method 1000 performs 3D reconstruction.

FIG. 11 is a functional block diagram of image system 1100 from one or more of the embodiments of the disclosed technology, including X-ray source 110, detectors 1120, and reconstruction apparatus 1130. X-ray source 110 is configured to emit a plurality of X-ray fanbeams. Detectors 1120 may comprise a plurality of columns of detectors 120, 130, and 140, wherein each column of detectors 120, 130, and 140 is arranged at a preset angle with respect to the X-ray source 110, and configured to detect a strength value of a respective one of the X-ray fanbeams penetrating an object under inspection and form a respective transmission image, when the object intersects, or moves along a direction intersecting with, the X-ray fanbeams. Reconstruction apparatus 1130 is configured to use any two of the formed transmission images as a binocular image, calculate depth information of the object on the transmission images, superpose and fuse the calculated depth information to obtain 3-Dimensional (3D) information, and perform 3D reconstruction.

It should be understood that any reference to an element herein using a designation such as "first," "second," and so forth does not generally limit the quantity or order of those elements. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements. In addition, terminology of the form "at least one of: A, B, or C" used in the description or the claims means "A or B or C or any combination of these elements."

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the disclosed technology may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware or any combination thereof. If implemented in software, the functions may be stored as one or more instructions on a computer-readable medium. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray® disc where disks usually reproduce data magnetically, while discs reproduce data optically with lasers.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

It is to be understood that the claims are not limited to the precise configuration and components illustrated above. Various modifications, changes and variations may be made in the arrangement, operation and details of the methods and apparatus described above without departing from the scope of the claims.

What is claimed is:

1. A stereoscopic imaging system, comprising:
an X-ray source configured to emit a plurality of X-ray fanbeams;
a plurality of columns of detectors, wherein each column of detectors is arranged at a preset angle with respect to the X-ray source, and configured to detect a strength value of a respective one of the X-ray fanbeams penetrating an object under inspection, and each column of detectors is configured to form a respective transmission image, when the object intersects, or moves along a direction intersecting with, the X-ray fanbeams, with the preset angle being unchanged; and
a reconstruction apparatus configured to select two transmission images from the formed transmission images, use the selected images to calculate depth information regarding the object and reconstruct a 3D image of the object based on the calculated depth information.

2. The stereoscopic imaging system according to claim 1, wherein using the selected images to calculate depth information comprises:

determining relative depth information of two feature points on the object by calculating a difference of point distances between the two feature points on the two transmission images; and obtaining depth information regarding the object based on relative depth information of feature points on the object.

3. The stereoscopic imaging system according to claim 1, wherein the reconstruction apparatus is configured to correct x and y image coordinates of points on the objects using the calculated depth information.

4. The stereoscopic imaging system according to claim 2, wherein the relative depth H between two feature points A and B is calculated by the following equation:

$$H = \frac{L}{2\tan(\alpha/2)}$$

wherein L is a difference of x-axis displacements from A to B on the two transmission images and α is a span angle of the two columns of detectors that formed the two selected images with respect to the X-ray source.

5. The stereoscopic imaging system according to claim 1, wherein the reconstruction apparatus is configured to identify a container in one of the formed transmission images, determine position and size of the container and reconstruct a 3D image of the container based on the position and size using a container model.

6. A method of stereoscopic imaging in a stereoscopic imaging system comprising an X-ray source and a plurality of columns of detectors, wherein each column of detectors is arranged at a preset angle with respect to the X-ray source, the method comprising:

emitting a plurality of X-ray fanbeams;

detecting, by each column of detectors, a strength value of a respective one of the X-ray fanbeams penetrating an object under inspection when the object intersects, or moves along a direction intersecting with, the X-ray fanbeams, with the preset angle being unchanged;

forming, by each column of detectors, a respective transmission image;

selecting two transmission images from the formed transmission images;

using the selected images to calculate depth information regarding the object; and reconstructing a 3D image of the object based on the calculated depth information.

7. The method according to claim 6, wherein using the selected images to calculate depth information regarding the object comprises:

determining relative depth information of two feature points on the object by calculating a difference of point distances between the two feature points on the two transmission images; and obtaining depth information regarding the object based on relative depth information of feature points on the object.

8. The method according to claim 6, wherein the calculated depth information is used to correct x and y image coordinates of points on the object.

9. The method according to claim 7, wherein the relative depth H between two feature points A and B is calculated by the following equation:

$$H = \frac{L}{2\tan(\alpha/2)}$$

wherein L is a difference of x-axis displacements from A to B on the two transmission images and a is a span angle of the two columns of detectors that formed the two selected images with respect to the X-ray source.

10. The stereoscopic imaging system according to claim 1, wherein the selected two transmission images are formed by two columns of detectors symmetrically placed with respect to a center line of a span angle of the plurality of X-ray fanbeams.

11. The stereoscopic imaging system according to claim 5, wherein the 3D image of the container is utilized in reconstructing the 3D image of the object.

12. The method according to claim 6, wherein the selected two transmission images are formed by two columns of detectors symmetrically placed with respect to a center line of a span angle of the plurality of X-ray fanbeams.

13. The method according to claim 6, wherein reconstructing the 3D image of the object based on the calculated depth information further comprises:

identifying a container in one of the formed transmission images;

determining position and size of the container; and reconstructing a 3D image of the container based on the position and size using a container model.

14. The method according to claim 13, wherein the 3D image of the container is utilized in reconstructing the 3D image of the object.

\* \* \* \* \*

UNITED STATES PATENT AND TRADEMARK OFFICE
CERTIFICATE OF CORRECTION

PATENT NO. : 9,763,630 B2  
APPLICATION NO. : 14/525078  
DATED : September 19, 2017  
INVENTOR(S) : Zhiqiang Chen et al.

Page 1 of 1

It is certified that error appears in the above-identified patent and that said Letters Patent is hereby corrected as shown below:

On the Title Page

Column 1, item (72), Inventor, delete "Zhuowen Tu, Beijing (CN);"

Signed and Sealed this  
Eighth Day of September, 2020

Andrei Iancu  
*Director of the United States Patent and Trademark Office*